US008697093B2

(12) United States Patent
Lanio Ruiz et al.

(10) Patent No.: US 8,697,093 B2
(45) Date of Patent: Apr. 15, 2014

(54) VACCINE COMPOSITION BASED ON STICHOLYSIN ENCAPSULATED INTO LIPOSOMES

(75) Inventors: Maria Eliana Lanio Ruiz, La Habana (CU); Luis Enrique Fernández Molina, La Habana (CU); Rady Judith Laboroe Quintana, La Habana (CU); Yoelys Cruz Leal, La Habana (CU); Maria del Carmen Luzardo Lorenzo, La Habana (CU); Circe Mesa Pardillo, La Habana (CU); Carlos Manuel Alvarez Valcárcel, La Habana (CU); Isabel Fabiola Pazos Santos, La Habana (CU); Mayra Tejuca Martínez, La Habana (CU); Aisel Valle Garay, La Habana (CU); Maria Eugenia Alonso Biosca, La Habana (CU); Liem Canet Santos, La Habana (CU)

(73) Assignee: Centro De Immunologia Molecular, La Habana (CU)

( * ) Notice: Subject to any disclaimer, the term of this patent is extended or adjusted under 35 U.S.C. 154(b) by 0 days.

(21) Appl. No.: 13/808,276

(22) PCT Filed: Jul. 5, 2011

(86) PCT No.: PCT/CU2011/000004
§ 371 (c)(1),
(2), (4) Date: Feb. 5, 2013

(87) PCT Pub. No.: WO2012/003814
PCT Pub. Date: Jan. 12, 2012

(65) Prior Publication Data

US 2013/0149376 A1 Jun. 13, 2013

(30) Foreign Application Priority Data

Jul. 6, 2010 (CU) .......................... CU/P/2010/144

(51) Int. Cl.
*A61K 9/00* (2006.01)
(52) U.S. Cl.
USPC .................................. 424/278.1; 424/450

(58) Field of Classification Search
None
See application file for complete search history.

(56) References Cited

U.S. PATENT DOCUMENTS 6,248,329 B1 * 6/2001 Chandrashekar et al. . 424/191.1
2010/0000152 A1 1/2010 Shinohara et al.

OTHER PUBLICATIONS

Ellis (Chapter 29 of Vaccines, Plotkin, et al. (eds) WB Saunders, Philadelphia, 1998.*

Alvarez et al., "Sticholysins, two pore-forming toxins produced by the Caribbean Sea anemone *Stichodactyla helianthus*: Their interaction with membranes", Toxicon, 2009, 54(8):1135-47.
Amacker et al., "Peptide-loaded chimeric influenza virosomes for efficient in vivo induction of cytotoxic T cells", Int'l Immunol., 2005, 17(6), 695-704.
Dietrich et al., From evil to good: a cytolysin in vaccine development:, Trends in Microbiology, 2001, vol. 9 No. 1, 23-28.
Kusmartsev et al., "Inhibition of myeloid cell differentiation in cancer: the role of reactive oxygen species", J Leukoc Biol., 2003, 74: 186-96.
Lanio et al., "Purification and characterization of two hemolysins from *Stichodactyla helianthus* ", Toxicon. 2001, 39, 187-94.
Lanio et al., "Humoral Immune Response Agains Epidermal Growth Factor Encapsulated in Dehydration Rehydration Vesicles of Different Phospholipid Composition", J Liposome Res.,2008,18(1),1-19.
Leserman, "Liposomes as in Carriers in Immunology", Journal of Liposome Research, 2004, 14 (3 & 4), 175-189.
Martinez et al., Properties of St I and St II, two isotoxins isolated from *Stichodactyla helianthus*: a comparsion Toxicon, 2001, 39,1547-1560.
Martinez et al., "Influencia Del estado De Fase De La membrana Sobre La asociacion De sticholysina II, Una Toxina Formadora De Poros De *Stichodactyla hilianthus* ", Revista Biologia, 2002, 16, 2: 85-93, abstract.
Martinez et al., Effect of sphingomyelin and cholesterol on the interaction of St II with lipidic interfaces, Toxicon 49 , 2007, 49: 68-81.
Moore et al., Introduction of Soluble Protein into the Class I Pathway of Antigen Processing and Presentation Cell 1988, 54: 777-85.
Moron et al., New tools for antigen delivery to the MHC class I pathway; Trends in Immunology, 2004, vol. 25 No. 2, 92-97.
Gluck et al., "Biophysical Validation of Epaxal Berna, a Hepatitis A Vaccine Adjuvanted with Immunopotentiating Reconstituted Influenza Virosomes (IRIV)", Dev Biol. (Basel), Karger, 2000, vol. 103, pp. 189-197.
Pazos et al., "Structural and functional charcterization of a recombinant sticholysin I (rSt I) from the sea anemone *Stichodactyla helianthus* ", Toxicon, 2006, 48, 1083-1094.
Penton et al., "Validation of a mutant of the pore-forming toxin sticholysin-I for the construction of proteinase-activated immunotoxins" Protein Eng Des Sel. 2011, 24, 485-493.
Schoen et al., Delivery of Foreign Substances to Cells Mediated by Fusion-Active Reconstituted Influenza Virus Envelopes (Virosomes), J. Liposome Res. 1993, 3: 767-792.

(Continued)

*Primary Examiner* — Brian J Gangle
(74) *Attorney, Agent, or Firm* — Rothwell, Figg, Ernst & Manbeck, P.C.

(57) ABSTRACT

The present invention relates to the field of biotechnology applied to human health. The invention describes a vaccine vehicle which toxins from eukaryotic organisms are encapsulated in liposomes with multiple lipid layers, obtained by means of the process of dehydration/rehydration, the lipid composition of which is dipalmitoylphosphatidylcholine: cholesterol in a molar ration of 1:1, which are designed for subcutaneous or intramuscular administration. These compositions do not require the use of other adjuvants. The compositions described allow modulation of the specific CTL immune response to one or more antigens co-encapsulated in the liposomes that containing the toxin. The vaccine vehicle of the present invention presents advantages as compared with others described in the prior art owning to the robust and functional nature of the immune response induced and also the immunomodulating properties thereof.

4 Claims, 6 Drawing Sheets

(56) References Cited

OTHER PUBLICATIONS

Schumacher et al., "Influenza virosomes enhance class I restricted CTL induction through CD4+ T Cell activation", Vaccine, 2004, 22: 714-723.

Zurbriggen et al., "IRIV-adjuvanted hepatitis A vaccine: in vivo absorption and biophysical characterization", Progr., in Lipid Res., 2000, 39, 3-18.

Zurbriggen et al., "Immunostimulating reconstituted influenza virosomes", Vaccine, 2003 14; 21(9-10):921-4.

* cited by examiner

VACCINE COMPOSITION BASED ON STICHOLYSIN ENCAPSULATED INTO LIPOSOMES

CROSS REFERENCE TO RELATED APPLICATION

This application is a 35 U.S.C. 371 National Phase Entry Application from PCT/CU2011/000004, filed Jul. 5, 2011, which claims the benefit of Cuban Patent Application No. CU/P/2010/144 filed on Jul. 6, 2010, the disclosure of which is hereby incorporated by reference.

REFERENCE TO A SEQUENCE LISTING

The present application includes a Sequence Listing filed in electronic format. The Sequence Listing is entitled "3035-0113_ST25.txt" created on Dec. 9, 2013, and is 1,000 bytes in size. The information in the electronic format of the Sequence Listing is part of the present application and is incorporated herein by reference in its entirety.

TECHNICAL FIELD

The present invention relates to the field of biotechnology applied to human health. Particularly, the present invention relates to a vaccine vehicle for use in both subcutaneous and intramuscular based on liposomes containing sticholysin and enhancing antigen-specific immune cellular responses, useful in cancer immunotherapy and treatment of diseases caused by intracellular pathogens.

PRIOR ART

The immunoadjuvant capacity of the liposomal vesicles has long been known. Rationality that exists in the use of liposomes in immunization and vaccine design is based on their ability to release antigenic molecule on antigen presenting cells (APC) and stimulate an immune response. The most important advantages of liposomes as immunoadjuvants are summarized in: (i) the ability to mimic pathogens carrying large amounts of antigen to APC, (ii) the possibility of co-encapsulating antigens with immunostimulatory molecules, (iii) the flexibility to modify its physicochemical properties for the purpose of more effective, and (iv) the fact of being biodegradable and nontoxic (Leserman in Journal of Liposome Research, 2004, 14 (3 & 4), 175-189). A challenge in the field of vaccinology is the enhancement of cellular immune response mediated by antigen-specific cytotoxic T lymphocytes CD8+ (CTL), with relevance for the prevention and treatment of diseases induced by intracellular pathogens and tumor cells. Liposomal vesicles can enhance a CTL response but not always effectively. Different strategies based on liposomal vesicles have been designed with the intention of streamlining this function; examples are acidic pH-sensitive liposomes, cationic liposomes, the inclusion of immunomodulators such as CpG and pore-forming toxins form bacteria. Despite the variety of publications, some of these strategies have had limited success in the induction of effective cellular immune responses or are disadvantaged and therefore require a better design before implementation.

The integration of viral membrane proteins in the liposomal membrane in order to promote membrane fusion under conditions of acid pH or proteolytic processing, has been another alternative for the development of vaccine vehicles. These vesicles known as virosomes have not only been used as parental virus vaccines, but have also been exploited as vehicles for vaccine antigens, bound or encapsulated to virosome (Zurbriggen en Vaccine, 2003 14; 21(9-10):921-4). Virosome particles known with abbreviation IRIV (immunopotentiating reconstituted influenza virosomes), containing proteins and lipids from the envelope of influenza virus, are the best example of this strategy and form the basis of the patent of the vaccine against hepatitis A (U.S. Pat. No. 5,565,203). However, this vaccine preparation was designed to enhance neutralizing antibody response against hepatitis A. Binding of hepatitis A virus inactivated and highly pure in the virosome membrane favored the processing and presentation of derived peptides by the classical pathway MHCII, as a result of the fusion process of the virosome and endosomal membranes in APCs (Glück y Wälti in Dev Biol (Basel), 2000, 103, 189-97). The evidence described suggest that antigen-virosomes physical association is important in the immunoadjuvant (Zurbriggen et al., Progr., in Lipid Res., 2000, 39(1), 3-18; Amacker et al., in Int Immunol., 2005, 17(6), 695-704).

Schumacher et al., in Vaccine 22:714-723, 2004, reported that IRIVs are able to enhance cellular mediated immune response. Particularly, Schumacher et al. demonstrated its adjuvant activity in the induction of CTL in vitro. This ability depended mainly on the stimulation of the reactivity of CD4+T cells specific to viral proteins. However, although the use of virosomes as adjuvants has many advantages such as low toxicity and high immunogenicity, one of the problems in current virosomal technology is the absence of procedures for the efficient encapsulation of solutes such as proteins, required for induction of a CTL response. A lipid concentration at which virosomes are produced (1 mM of lipid, approximately), and considering its diameter (about 200 nm), less than 1% of the aqueous phase is encapsulated within the virosomes (Schoen et al., en J. Liposome Res., 3: 767-792, 1993). These features significantly reduce the efficiency of virosomes to release antigens or genes to cells. One strategy to overcome this limitation and to produce immunogenic preparation for CD8+T cells, recently published in the U.S. patent application number 20100015214, is based on a combination of empty virosomes with vehicles, preferably liposomes, which encapsulate antigens. U.S. 20100015214 discloses a trans-adjuvant effect of virosomes, although these particles and the liposomes do not exhibit any physical interaction between them.

In the article by Lanio. et al. published in the J Liposome Res., 2008, 18(1), 1-19 is described, for rhEGF, higher encapsulation-retention efficiency of liposome obtained by the dehydration-rehydration procedure (DRVs) and comprised of phosphatidylcholine (PC) saturated (dipalmitoylphosphatidylcholine, DPPC) and cholesterol (Cho) in molar ratio 1:1 compared with those containing unsaturated PC and Cho. In fact, the procedure for obtaining DRVs yields multi-bilayer vesicles with high encapsulation/retention efficiency for a wide variety of soluble solutes. Lanio et al. demonstrated the immunoadjuvant properties of these vesicles to enhance an antibody response quantitatively and qualitatively superior against rhEGF.

The review published by Alvarez et al. in Toxicon, 2009, 54(8):1135-47, summarizes the structural and functional characteristics of two proteins produced by a marine invertebrate, the Caribbean Sea anemone *Stichodactyla helianthus*, and named by the authors Sticholysins (Sts) I and II (StI/II). These proteins are pore-forming toxins (PFTs) belonging to the protein family Actinoporins, unique classes of PFTs of eukaryotic origin found exclusively on sea anemones. Similar to other members of this family, Sts are basic proteins with high isoelectric point (>9.5), with molecular mass of approximately 20 kDa, devoid of cysteine residues in their amino acid sequences and exhibiting a preference for membranes containing sphingomyelin (SM). Sts are produced in soluble form but can easily associate with different cellular and model membrane systems forming pores with a diameter of 2 nm, probably due to the interaction of the N-terminal's α helices from four monomers. Both events, the association and pore formation, depend on the physicochemical properties of membranes.

In the article published in Toxicon, 2007, 49: 68-81, Martinez et al. reports the relevance of the presence of SM and Cho for the association and pore-formation in the membranes by StII. The phase state of the membrane influences the StII association with these structures. As reported by Martinez et al., in the journal Biology, 2002, 16, 2:85-93, this toxin is associated reversibly to membranes of DPPC and SM, with a very low capacity of permeabilization.

Although widely reported the immunomodulatory properties of pore-forming toxins from bacteria for the induction of antigen-specific CTL response, using different strategies including their encapsulation into liposomes, as summarized in reviews by Dietrich et al. and Morón et al., in TRENDS in Microbiology, 2001, Vol. 9 No. 1, 23-28 and TRENDS in Immunology, 2004, Vol. 25 No. 2, 92-97, respectively; nothing has been referred to the functionally homologous toxins from marine eukaryotic organisms.

From the point of view of their applications in immune therapy of tumor diseases, it is desirable to have new vaccine formulations able of inducing specific cellular immune response to antigens and are less aggressive than those compositions containing bacterial toxins.

BRIEF DESCRIPTION OF THE INVENTION

Surprisingly, the authors of the present invention have found that when an antigen is administered subcutaneously (sc) or intramuscularly (im) encapsulated in the vaccine formulation Liposome-St, with any of the variants of toxins described including those that do not exhibit pore-forming or lytic activity, much higher percentages of lysis of target cells are induced than those observed in the positive control group using Polyinosinic:polycytidylic acid (poly I:C, PIC) which is considered in the state of the art as the quintessential enhancer of CTL response, unmodified antibody levels and mixed Th1/Th2 response induced by the liposomal antigen. This indicates the potential of liposome-St system to generate both cellular and humoral response against a protein antigen, which is relevant to the use of this formulation for vaccination purposes.

The object of this invention is a vaccine vehicle based on liposomal preparations of DPPC and Cho co-encapsulating toxins known as Sts along with a protein antigen. Liposomal preparations of DPPC and Cho in which are encapsulated mutants of toxins known as Sts (eg StIW111C and StIW111Cirrev) together with protein antigen are also the subject of the present invention.

In another aspect, the vaccine compositions based on this vaccinal vehicle containing the toxins together with an antigen administered sc or im for induction of a strong antigen-specific CTL response are also the subject of the present invention.

Another object of this invention is the use of the vaccinal compositions described, based on this vaccine vehicle containing the toxins together with an antigen and administered sc or im for strengthening of the immune response of a patient suffering from a disease selected from the group consisting of cancer and infectious diseases caused by intracellular pathogens.

In another aspect the subject of the present invention is also a method for treating patients who require a strengthening of their immune response, wherein the patient suffers from a disease selected from the group consisting of cancer and infectious diseases caused by intracellular pathogens and wherein the method comprises administering sc or im the vaccinal compositions based on this vaccine vehicle containing the toxins Sts or their mutants together with a relevant antigen for the disease.

Additionally, the present invention also relates to the protection provided by such vaccine compositions to the challenge with tumor cells expressing the antigen, reducing the percentage of tumors and increasing survival of subjects with tumors. Therefore, a prophylactic method of onset of illness related to the antigen is also an object of this invention.

DETAILED DESCRIPTION OF THE INVENTION

The vaccine vehicle of the invention is based on aqueous dispersions of DRV liposomes of DPPC:Cho: in a 1:1 molar ratio that encapsulate St together with antigen, and eventually can contain other co-solvents miscible with water, no toxic, non-irritating and do not cause destabilization of the vesicles, such as those commonly used in injectable pharmaceutical compositions, for example sugars, polyethylene glycol, etc. Liposomal preparations of the present invention are obtained by the dehydration-rehydration procedure and constituted by DPPC and Cho in a 1:1 molar ratio and co-encapsulating an antigen with some of the Sts variants or their reversibly inactive mutants, wherein said vaccinal compositions are able to promote an antigen-specific CTL immune response and protective against challenge with tumor cells.

In one embodiment of the invention the vaccine composition contains as antigen the protein OVA, but wherein the antigen can be any protein or polypeptide associated to a disease for which, from a therapeutic standpoint, is relevant induce a specific CTL immune response against this protein antigen. For example, the antigen may be a protein or polypeptide associated with cancer, a protein or polypeptide associated with AIDS or a protein or polypeptide associated with tuberculosis.

The liposomes described herein are obtained by dehydration-rehydration technology reported by Kirby and Gregoriadis in Biotechnology, 1984, 2, 979-984, these are vesicles with an internal aqueous phase surrounded by several lipid bilayers characterized by high efficiency of encapsulation and retention of labile molecules such as antigen and immunomodulator proteins. Chloroform solutions of DPPC and Cho in a 1:1 molar ratio are evaporated and kept under vacuum for 30 minutes. The lipids were hydrated with deionized water at a temperature above the phase transition temperature (Tc) of DPPC (T>45° C.). Suspensions of multilamellar vesicles resulting (MLVs) are transformed in SUV or LUV (Small Unilamellar Vesicles and Large Unilamellar Vesicles, respectively) by ultrasound and rest cycles or extrusion through polycarbonate membranes of pore size 100 nm. The vesicles obtained were mixed with protein solutions, following a relationship lipid: protein from 16-64 μmol of lipids: 1.8-7 nmol of antigen and 0.5-2 nmol of St, and lyophilized for 20-24 hours. Rehydration was performed with deionized water and stirring for 30 minutes at a temperature less than 45° C. The material unencapsulated in liposomes is removed by washing with phosphate buffered saline (PBS) pH 7.4 (NaCl 136 mmol/L, $KH_2PO_4$ 1.47 mmol/L, Na2HPO4 9.55 mmol/L, KCl 2.68 mmol/L) followed by centrifugation at 10 000 g for 15 min. Such preparations reach encapsulation efficiency for the different variants of Sts ranging around 50% with retention of 70% after one month of storage at 4° C. suspended in PBS.

StI and StII toxins are isolated and purified from the sea anemone *Stichodactyla helianthus*, using the procedure described by Lanio et al. in Toxicon. 2001, 39, 187-94. The recombinant Sticholysin I (rStI) and rStI mutant, StI W111C, are obtained according to the procedures described by Pazos et al. in Toxicon, 2006, 48, 1083-1094 and Pentón et al. in Protein Eng Des Sel. 2011, 24, 485-493, respectively.

The concentration of Sts used in the vaccine vehicle of the present invention is in the range of 0.25 to 1 μM co-encapulated with antigen in a concentration range of 1-3.5 μM in a liposomal suspension with a range of total lipid concentration of 16 to 64 mM. Preferably the vaccine vehicle of the present invention contains an amount of Sts of 0.3 to 0.4 nmol co-encapulated with 1 to 2 nmol of antigen in a liposomal suspension of 20 μmol of total lipids in a volume of 200 μL.

The dose range used for the vaccines referred to in the present invention, by sc or im, is 1-2 nmol (50-100 mg) of antigen.

A key feature of the vaccine compositions of the invention is that they lack immunological adjuvants other than those described.

As already explained above, it is known from the prior art that bacterial pore-forming toxins encapsulated into liposomal vesicles are able to enhance a CTL response, but it is known that use of vaccine compositions based on bacterial toxins have adverse effects on human; however, the authors of the present invention have found unexpectedly that non-bacterial toxins are able to have the same immunostimulator effect. Moreover, the authors of this invention have managed to decouple the pore-forming activity of the toxins from their stimulator effects of the CTL response, which offers great advantages for clinical use in humans to this vaccine vehicle. The results obtained using in the vaccine vehicle of the present invention the molecular entities StIW111$C_{irrev}$ or heat-inactivated StII co-encapsulated with antigen into liposomes, demonstrate that there is no absolute dependence between the enhancement of an antigen-specific CTL immune response by the formulations of liposome-St and the ability of these proteins to form pores in membranes. The test of maturation of dendritic cells (DCs) isolated from bone marrow of C57BL/6 mice and exposed to StII in vitro, shows the ability of this protein not only in its active variant, but also in that heat-inactivated, to induce the activation of CDs, similar to that seen with LPS (positive control) under similar conditions.

The ability of Sts to form pores in membranes was assessed by testing hemolytic activity and permeability of LUVs loaded with carboxyfluorescein (CF) as described by Martinez et al. in Toxicon, 2001, 39,1547-1560. It was shown that Sts do not exhibit permeabilizing activity by analyzing permeability of liposomal vesicles of DPPC:Cho (1:1) encapsulating CF, compared with that observed in vesicles composed of egg yolk phosphatidylcholine and SM (1:1) (positive control).

It was verified that the mutant StIW111C forms an inactive dimer stabilized by a disulfide bond by the hemolytic activity assay and SDS-PAGE in the presence and absence of 2-mercaptoethanol (2-ME) as reducing agent, just as described by Pentón et al. in Protein Eng Des Sel. 2011, 24, 485-493. The inability of dimeric structure to form pores in erythrocytes, as model cells, was result of its non-association with membrane.

A procedure to obtain an irreversible dimeric specie of StIW111C (StIW111$C_{irrev}$) based on the reduction of StIW111C by incubation with 2-ME (0.1 mol/L), elimination of reducing agent by filtration on column PD-10, and immediate incubation of StIW111$C_{monomer}$ with the homobifunctional reagent bis (maleimide) hexane (BMH) in a molar ratio StIW111$C_{monomer}$:BMH 1:1 ó 2:1 for 2 hours at 4° C., was established. StIW111$C_{irrev}$ was purified by gel filtration chromatography on column SUPERDEX™ 75 HR 10/300 (a gel filtration column containing dextran to highly cross-linked porous agarose beads) in the presence of a reducing agent. The obtaining of the irreversible dimer and its purity degree were verified by SDS-PAGE under reducing conditions. The irreversible dimer was obtained with 94% purity and only 6% contaminant of the reversible dimer. The absence of functional activity was verified by hemolytic activity assay.

StII irreversible inactivation by heat treatment was performed according to the procedure described by Martinez et al. in Toxicon, 2001, 39,1547-1560 and the total loss of the ability to form pores in the membrane was checked by hemolytic activity assay.

The immunomodulator properties of the different molecular species Sts in the system liposome-St related to its ability to enhance an antigen-specific cytotoxic immune response in vivo and antitumor immunity in a preventive scenary, can be measured in the experimental model of the mice strain C57BL/6 using the antigen OVA and the tumor cell line E.G7, a subclone of murine EL-4 thymoma (Kusmartsev y Gabrilovich, in J Leukoc Biol., 2003, 74: 186-96), transfected with complementary DNA of OVA pAc-neo-OVA (Moore, et al. in Cell, 1988, 54: 777-85) and obtained from "*American Type Cultures Collection*" (ATCC, VA).

The authors of the present invention have also found that preventive inoculation with the vaccinal vehicle liposomes-St containing antigen induces antitumor protection higher than that generated by liposomes containing no StII.

These results demonstrate that the system liposome-St is effective to induce an antitumor response functionally robust and protective, when using a protein antigen, without the need for other adjuvants. In turn, the use of this preparation in combining therapies may further enhance its antitumor effect.

In the following examples it is included comparative experimental details that allow verifying the immunological efficacy of inducing an antigen-specific cytotoxic immune response in vivo and antitumor immunity in a preventive scenary of the vaccinal compositions object of the invention with regard to the other non-liposomal formulations and do not contain Sts.

EXAMPLES

Example 1

Assessment of Cytotoxicity and CTL Response of the Vaccinal Vehicle Using Native StI Or StII And OVA As Protein Antigen.

The vaccinal vehicle based on liposomes was prepared as previously described.

In DRVs vesicles comprised of DPPC and Cho (molar ratio 1:1), OVA as model antigen and Sts (StI or StII) were co-encapsulated in a 10 μmol of total lipids: 1.1 nmol OVA and 0.3 nmol of St molar ratio in phosphate buffer saline (PBS) pH 7.4. Following this procedure, two vacinal compositions were obtained:

Vaccinal Composition A: DRVs liposomes of DPPC:Cho (60 µmol of total lipids) encapsulating 6.6 nmol (50 µg) of OVA.

Vaccinal Composition B: DRVs liposomes of DPPC:Cho (60 µmol of total lipids) co-encapsulating 6.6 nmol (50 µg) of OVA and 1.88 nmol of StI or StII.

Fifteen C57BL/6 female mice with a body weight ranging from 18-20 g were selected and separated into 5 experimental groups of three animals each.

Group 1 (negative control) was inoculate by sc route on days 0, 12, 13 and 14, with 0.2 mL phosphate buffered saline (PBS).

Group 2 (positive control) was inoculated by sc route, on day 12, with 22.2 nmol (1 mg) of OVA and mixtured with 100 µg of polyinosinoic-polycitidilic acid (PIC), a TLR3 synthetic ligand and a classical inductor of CTL response (Hamilton-Williams et al. in J. Immunol., 2005, 174: 1159-63), on days 13 and 14 the animals received again 100 µg of PIC.

Group 3 was inoculated by sc route on days 0 and 12, with 0.2 mL of vaccinal composition A (equivalent to a 1.1 nmol or 50 µg of OVA).

Group 4 was inoculated by subcutaneous route on days 0 and 12, with 0.2 mL of vaccinal composition B (equivalent to 1.1 nmol or 50 µg of OVA and 0.3 nmol or 6.25 µg of StI).

Group 5 was inoculated by sc route on days 0 and 12, with 0.2 mL of vaccinal composition B (equivalent to 1.1 nmol or 50 µg of OVA and 0.3 nmol or 6.25 µg of StII).

On day 20 of the experiment, spleen cells from C57BL/6 non-immunized mice were incubated with two concentrations of carboxy-fluorescein diacetate succinimidyl ester (CFSE) (0.33 y 5 µmol/L, respectively); the labeled cells with the highest fluorescence intensity were also incubated with 1 µmol/L of OVA (257-SEQ ID NO: 1: SIINFEKL-264) immunodominant peptide in the context of the MHC I haplotype for C57BL/6 mice strain. Afterwards, both populations of labeled cells were mixed 1:1 and the experimental groups 1-5 were inoculated by the tail vein with $30 \times 10^6$ cells of the mixture in 0.2 mL total volume. Mice were sacrificed after 16 hours and lysis (%) of the target cells was determined in the inguinal lymph node closer to the immunization site by flow cytometry (FACS).

FIG. 1 shows the cytotoxicity produced in vivo by immunization of mice with liposomes co-encapsulating OVA and Sts. The immunized animals with liposomes co-encapsulating Sts (StI or StII) showed a CD8+T cytotoxic lymphocyte response (CTL) specific to OVA stastically higher than the positive control group. Additionally, liposomes that only contained OVA also induced a CTL response statistically similar to the classical positive control for this assay (PIC).

Example 2

Induction of Antitumoral Protection of the Vaccinal Vehicle in the OVA Protein Model.

The ability of the liposome-based vaccines to induce antitumoral protection was studied. To this end, sixty C57BL/6 female mice with a body weight ranging between 18-20 g were selected and separated into 3 assay groups of 20 animals each.

Group 1 (negative control) was inoculated by im route, on days 0 and 12, with 0.2 mL of phosphate buffer saline (PBS).

Group 2 was inoculated by im route, on days 0 and 12, with 0.2 mL of the vaccinal composition A described in example 1 (equivalent to 1.1 nmol or 50 µg of OVA).

Group 3 was inoculated by im route, on days 0 and 12, with 0.2 mL of the vacinal composition B described in example 1 (equivalent to 1.1 nmol or 50 µg of OVA and 0.3 nmol or 6.25 µg of StII).

All the Groups 1 to 3 were challenges on day 19 with $3 \times 10^5$ cells from the tumor line E.G7 by subcutaneous route (0.2 mL).

Animals were individualized from day 0 and the following parameters were determined thrice per week: tumor volume, time to progression and survival.

The results obtained are described below:

Time to progression

The time to progression is a parameter that characterizes the time elapsed for each animal from the moment the tumor is inoculated until its appearance. As for mice that had not developed a tumor at the end of the experiment, it was considered that the time to progression was 60 days. The impact on the extension of the time to progression is a highly desirable parameter for a vaccine against cancer. As it can be observed in FIG. 2A, animals from group 3, vaccinated with the formulation vaccinal composition B described in Example 1 and object of the invention, showed the most outstanding results Survival This parameter assesses the ability of vaccination to increase the time that immunized animals live upon challenged with the OVA-expressing tumor cells (E.G7). This parameter is measured in days and has a relative character, since it is compared with survival of non-treated animals. In order to prove the statistical significance of the differences found in survival results among groups the Log-Rank test was used.

FIG. 2B clearly shows that animals from group 3, vaccinated with the vaccinal composition B described in example 1 and object of the present invention are those that survive longer after tumor inoculation.

Example 3

Hemolytic Activity of Sts Mutants.

Pore-formation in erythrocyte membrane produces a colloid osmotic shock that brings about cell lysis. Pore-forming ability of the so called porins can be followed by its hemoleytic activity (HA) which can be experimentally determined by measuring the loss of apparent absorbance ($\lambda=600$ nm) of an erythrocyte suspension due to cell lysis.

In the assay, the HA of the StIW111C irreversibly inactive dimer (StI W111Cirrev) was compared with that of the reversible dimer StIW111C, in reducing (2-ME 0.1 mol/l) and non-reducing conditions, at a relatively high protein concentration in the assay (0.15 µmol/l), if compare with the HA of StI/StII reported by Álvarez et al. in Toxicon, 2009, 54(8): 1135-47. The time-courses of hemolysis shown in FIG. 3 indicate that StIW111C$_{irrev}$ was inactive under non-reducing conditions. Under reducing conditions, StIW111C$_{irrev}$ showed less activity than StIW111C either completely reduced or non-reduced.

Example 4

Assessment of the Pore-Forming Ability of Inactivated StII.

The loss of the ability to form pores in membranes by StII irreversibly inactivated by heating at 80° C. for two hours was registered using the hemolytic activity test. FIG. 4 shows the lack of hemolytic activity for the thermal-inactivated StII when compared to the active protein.

Example 5

Effect of the Vaccinal Vehicle on DCs Maturation.

Maturation of DCs induced by SW was assessed in cells obtained from the bone marrow of C57BL/6 mice exposed to active StII (0.1 nmol or 2 µg) or inactivated by thermal treatment (4 µg) in the presence or not of 20 µg of polymyxin B (pmxB, a neutralizing agent of endotoxin's biological activity by binding to lipid A fraction of LPS), for 24 hours at 37° C. in a 5% $CO_2$ chamber.

As positive control, it was used LPS (2 µg) and the negative control was RPMI medium plus 30 pmxB. Cells extracted from mice bone marrow were cultured in a number of 600 000 DCs precursors on RPMI per well using 6 wells plates. Bovine fetal serum (BFS) at 10%, 400 µL of GMCSF and RPMI were added to complete 3 mL per well.

FIG. 5 shows the increase (%) in the molecular markers (CD80, CD86 y CD40) indicative of DCs activation as a result of the exposition of these cells in vitro to both the active and the heat-inactivated StII variants, results comparable to those obtained with the positive control.

Example 6

Assessment of Cytotoxicity and CTL Response of the Vaccinal Vehicle Using St Mutants And OVA, As Antigen Protein.

The StI dimeric variants of reversibly (StIW111C) or irreversibly ($StIW111C_{irrev}$) low pore-forming activity and the thermal inactivated StII variant were co encapsulated with OVA into liposomes of DPPC:Cho (1:1), in a ratio 10 µmol total lipid: 1.1 nmol OVA: 0.3 nmol of StIW111C, $StIW111C_{irrev}$ or heat-inactivated StII, in PBS pH 7.4 and the ability of these vaccine preparations to induce an OVA-specific cytotoxic activity in vivo was assessed. In these assays, essentially the same vaccinal compositions were used as those described in Example 1, in the case of composition B, the different variants of St were employed.

Vaccine composition A: DRVs liposomes of DPPC:Cho (60 µmol of total lipids) encapsulating 6.6 nmol of OVA.

Vaccine composition B: DRVs liposomes of DPPC:Cho (60 µmol of total lipids) co-encapsulating 6.6 nmol of OVA and 1.875 nmol of St (StIW111C, $StIW111C_{irrev}$, native St II or heat-inactivated StII)

In a first assay, twelve female mice C57BL/6 were selected with a body weight between 18-20 g, and separated into 4 experimental groups of three animals each.

Group 1 (negative control) was inoculated by subcutaneous route, on days 0 and 12, with 0.2 mL of PBS.

Group 2 (positive control) was inoculated by subcutaneous route, on days 0 and 12, with 0.2 mL of the vaccinal composition B (equivalent to 1.1 nmol or 50 µg of OVA and 0.3 nmol or 6.25 µg of native StII).

Group 3 was inoculated by subcutaneous route, on days 0 y 12, with 0.2 mL of the vaccinal composition B (equivalent to 1.1 nmol or 50 µg of OVA and 0.3 nmol or 6.25 µg of StIW111C).

Group 4 was inoculated by subcutaneous route, on days 0 and 12, with 0.2 mL of the vaccinal composition B (equivalent to 1.1 nmol or 50 µg of OVA and 0.3 nmol or 6.25 µg of $StIW111C_{irrev}$).

FIG. 6A shows that animals immunized with liposomes containing St variants of low pore-forming activity (LP/OVA+StIW111C or LP/OVA+StIW111Cirrev) exhibit a cytotoxic response statistically similar to that obtained with StII when co-encapsulated with OVA into liposomes (LP/OVA+StII).

In other assay, nine female mice C57BL/6 with a body weight between 18-20 g were selected and separated into 3 groups of 3 animals each.

Group 1 (negative control) was inoculated by subcutaneous route, on days 0 and 12, with 0.2 mL of saline phosphate buffer (PBS).

Group 2 was inoculated by subcutaneous route, on days 0 and 12, with 0.2 mL of vaccinal composition A (equivalent to 1.1 nmol or 50 µg of OVA).

Group 3 was inoculated by subcutaneous route, on days 0 and 12, with 0.2 mL of vaccinal composition B (equivalent to 1.1 nmol or 50 µg of OVA and 0.3 nmol or 6.25 µg of inactive StII).

FIG. 6B evidences that immunization with liposomes co-encapsulating OVA the completely heat-inactivated StII variant elicited an OVA-specific cytotoxic activity significantly higher than that induced by liposomes containing only the antigen and similar to that observed with the liposomal formulation containing native StI/StII.

The experimental results demonstrated that the liposomal vaccine object of this invention co-encapsulating an antigen with any sticholysin variant, even with those that do not display pore-forming activity, induced a potent, robust and functional antigen-specific CTL response, even larger than that elicited by the classical positive control (PIC) used in an in vivo CTL assay. The formulation liposome-St on a preventive scenario significantly increased the time-course of tumor implantation and significantly increase survival in the groups evaluated in relation to those that only received PBS. In summary, vaccination with liposomes-St exhibited better results than those observed with liposomal vesicles only containing the antigen.

Graphic A: Percentage of CD80
Graphic B: Percentage of CD86
Graphic C: Percentage of CD40

Figure 1:
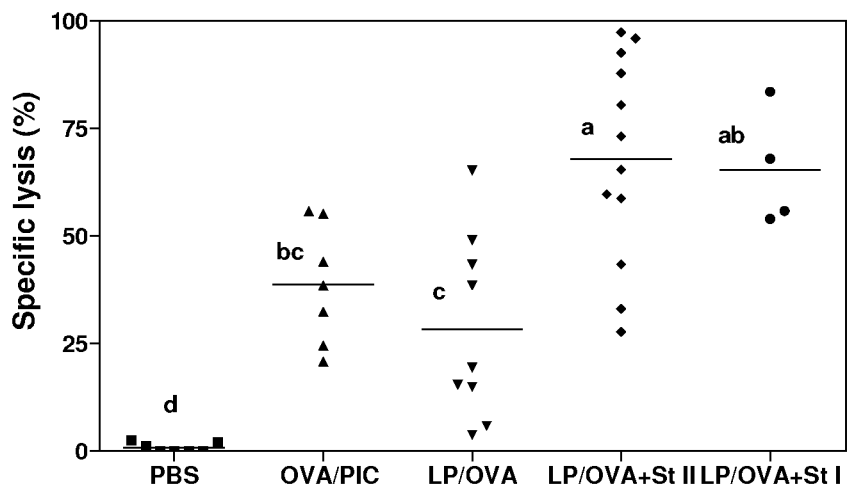
FIG. 1: represents a graphics showing lysis percentage of the target cells loaded with OVA-immunodominant peptide SEQ ID NO: 1 (SIINFEKL) and labeled with CFSE in experimental animals subjected to different vaccine treatments in an in vivo cytotocity assay. Each point corresponds to data from a single animal and the line to the mean value of at least two independent experiments. Different letters indicate significant statistical differences among immunized groups according to Dunnett T3 test (p<0.05).
Figure 2A:
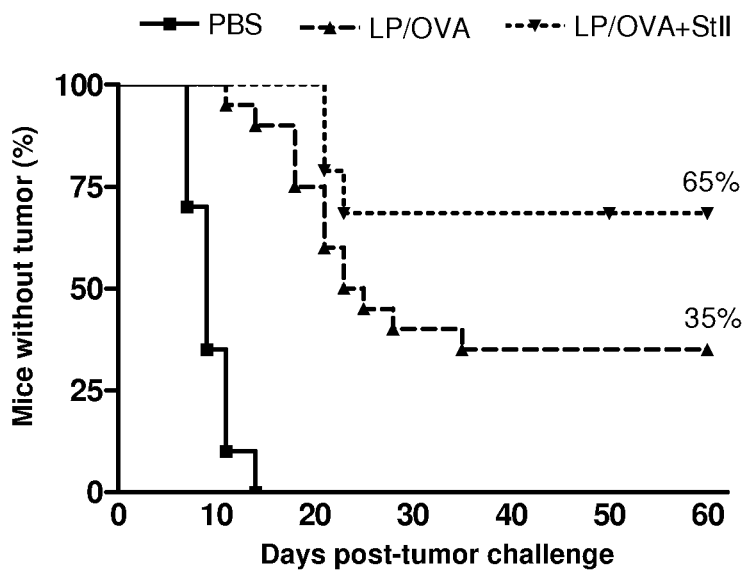
FIG. 2A: represents the percentage of animals free of tumor in three groups of experimental animals subjected to different vaccine treatments and challenged with OVA-expressing tumor cells.
Figure 2B:
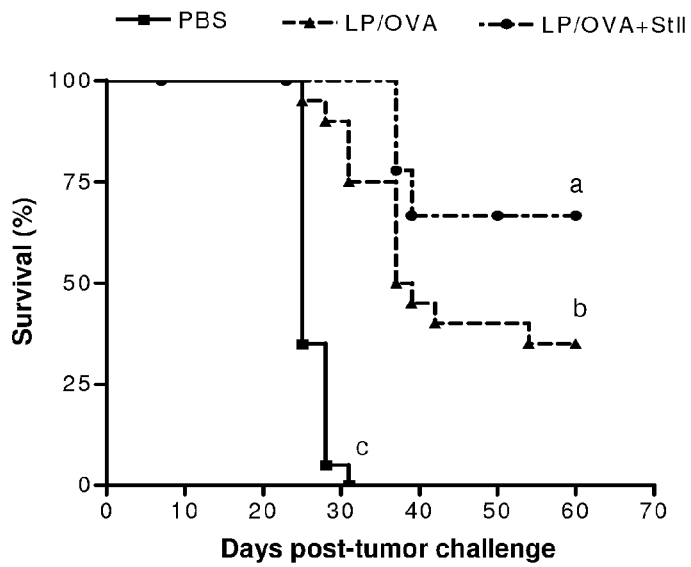
FIG. 2B: represents a graphic that allows visualizing the survival parameter in the three mentioned groups after inoculation of the OVA-expressing tumor cells. Different letters indicate significant statistical differences according to the Log-Rank test (p<0.05).
Figure 3:
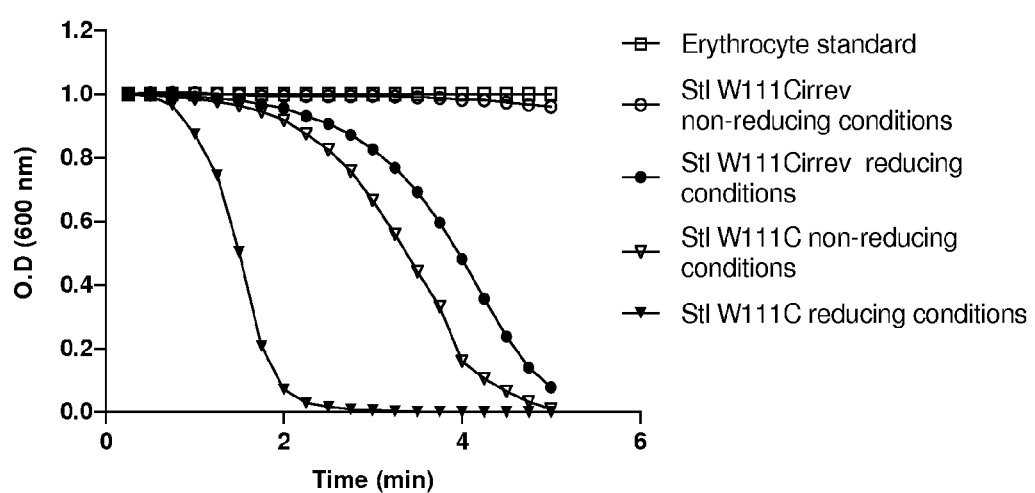
FIG. 3: shows variation in turbidity of an erythrocyte suspension due to the action of dimeric variants of StI (StIW111C o $StIW111C_{irrev}$) under reducing- (in the presence of 2-ME) and no reducing conditions.
Figure 4:
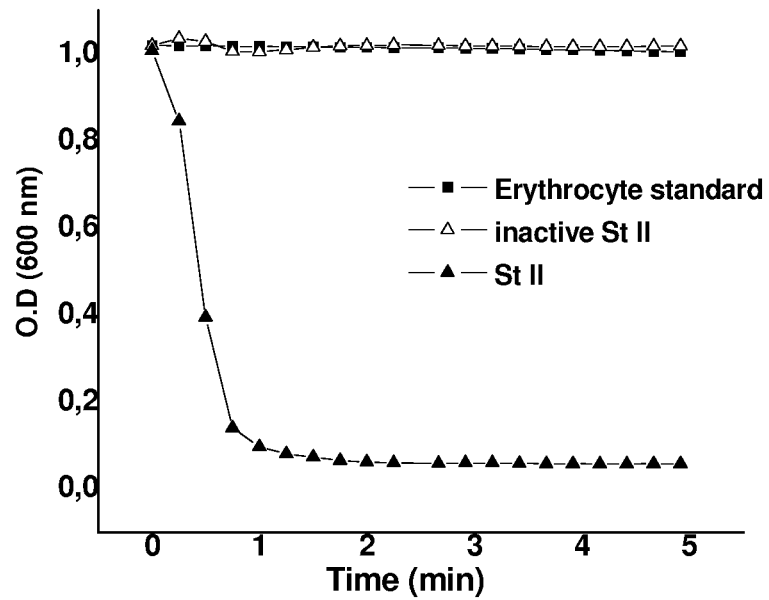
FIG. 4: represents loss of turbidity of an erythrocyte suspension due to the activity of native StII (active protein) or inactivated by thermal treatment.
Figure 5A:
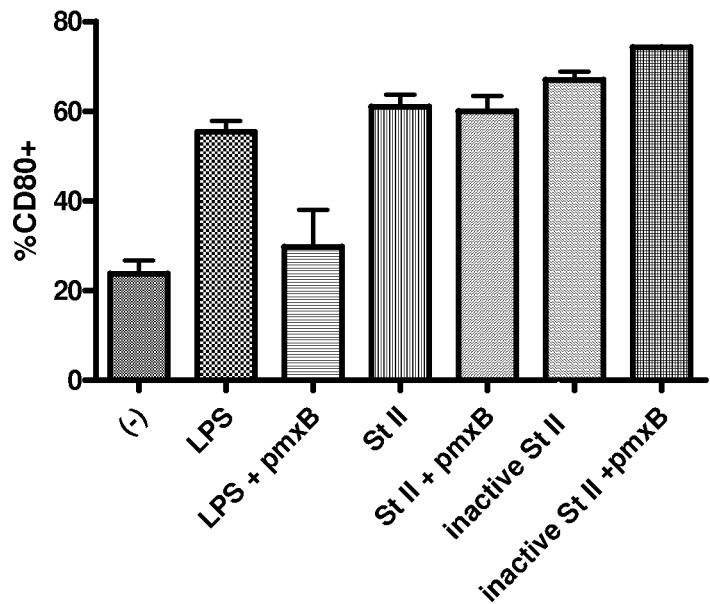
FIG. 5: shows changes in the expression of molecular markers of dendritic cells (DCs) due to their exposition in vitro to St II both in its active and thermal-inactivated variant in the presence or not of an endotoxin neutralizing agent (pmxB).
Figure 5B:
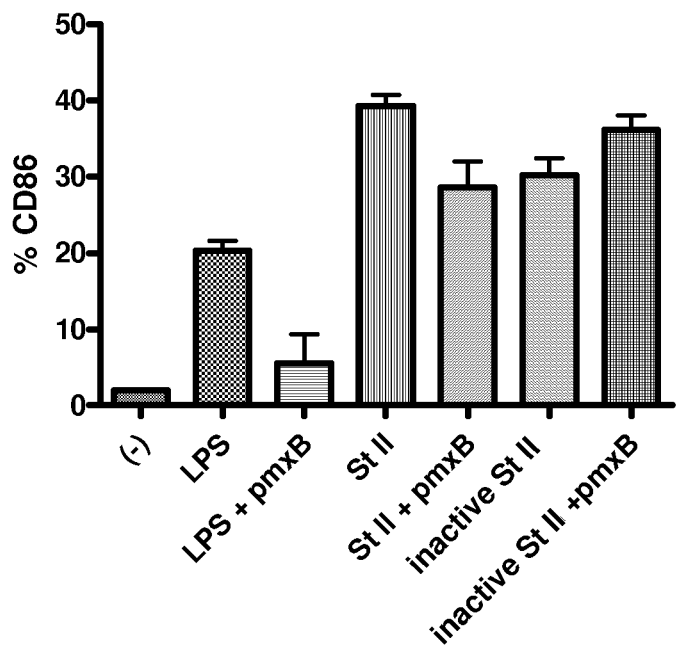
Figure 5C:
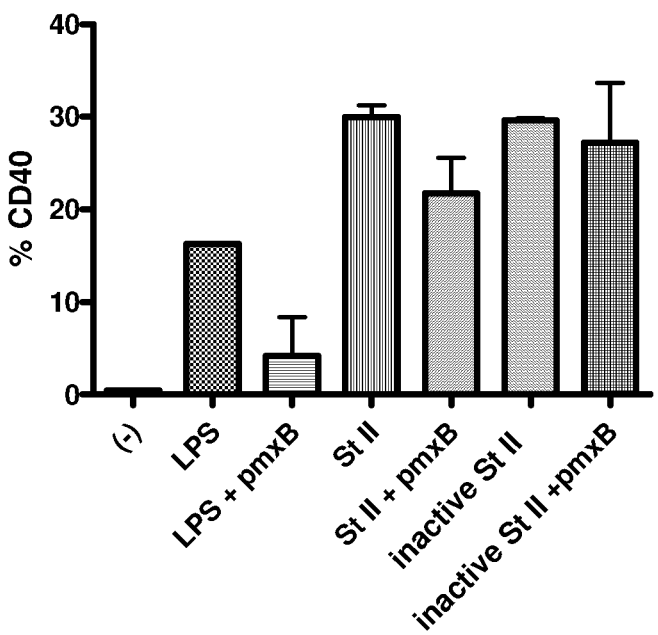
Figure 6A:
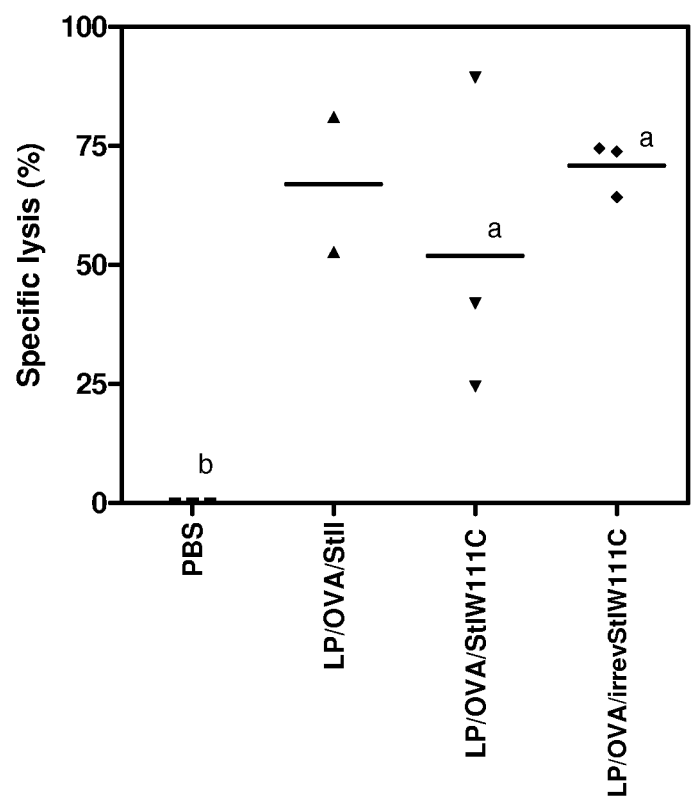
Figure 6B:
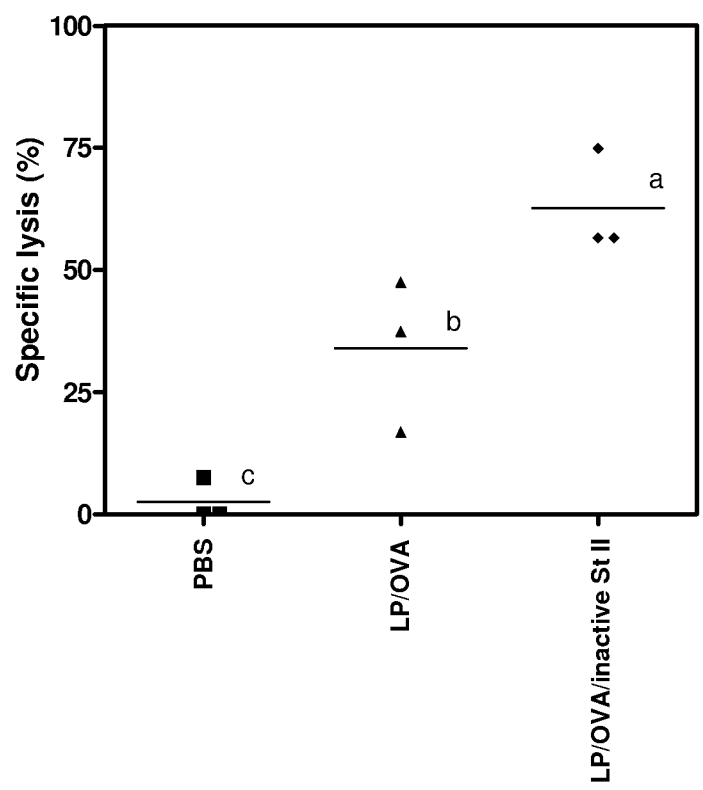

FIG. 6: represents two graphics showing lysis percentage of target cells loaded with OVA-immunodominant peptide SEQ ID NO: 1 (SIINFEKL) and labeled with CFSE in experimental animals subjected to different vaccine treatments in an in vivo cytotoxicity assay. Each point corresponds to data from a single animal and the line the mean value. Different letters indicate significant statistical differences among the immunized groups according to the Tukey test ($p<0.05$).

Graphic A: Response obtained upon immunización with liposomes co-encapsulating OVA, native StII or dimeric variants of StI reversibly- (StIW111C) or irreversibly (StIW111Cirrev) inactive.

Graphic B: Response obtained upon immunización with liposomes co-encapsulating OVA and StII inactivated by thermal treatment.

The invention claimed is:

1. A vaccine composition comprising an antigen and proteins obtained from *Stichodactyla helianthus* selected from the group consisting of Sticholysin I (StI), Sticholysin II (StII), Sticholysin I mutant W111C (StIW111C), StIW111C irreversibly inactivated dimer (StIW111Cirrev) and heat-inactivated StII, wherein the antigen and the proteins are encapsulated in a liposomal vesicle that contains dipalmitoylphosphatidylcholine (DPPC) and cholesterol (Cho) in an equimolar ratio.

2. The vaccine composition of claim 1, wherein the antigen is a protein or a polypeptide which induces a specific cytotoxic T lymphocyte immune response against cancer.

3. The vaccine composition of claim 1, wherein said vaccine composition does not contain any other immunological adjuvants.

4. A method of enhancing an immune response in a patient suffering from cancer, comprising administering to said patient an effective amount of the vaccine composition of claim 3.

* * * * *

```
SEQUENCE LISTING

<160> NUMBER OF SEQ ID NOS: 1

<210> SEQ ID NO 1
<211> LENGTH: 8
<212> TYPE: PRT
<213> ORGANISM: Mus musculus

<400> SEQUENCE: 1

Ser Ile Ile Asn Phe Glu Lys Leu
1               5
```